Feb. 11, 1941. F. H. HOWARD Plant Pat. 447
ROSE PLANT
Filed July 27, 1940
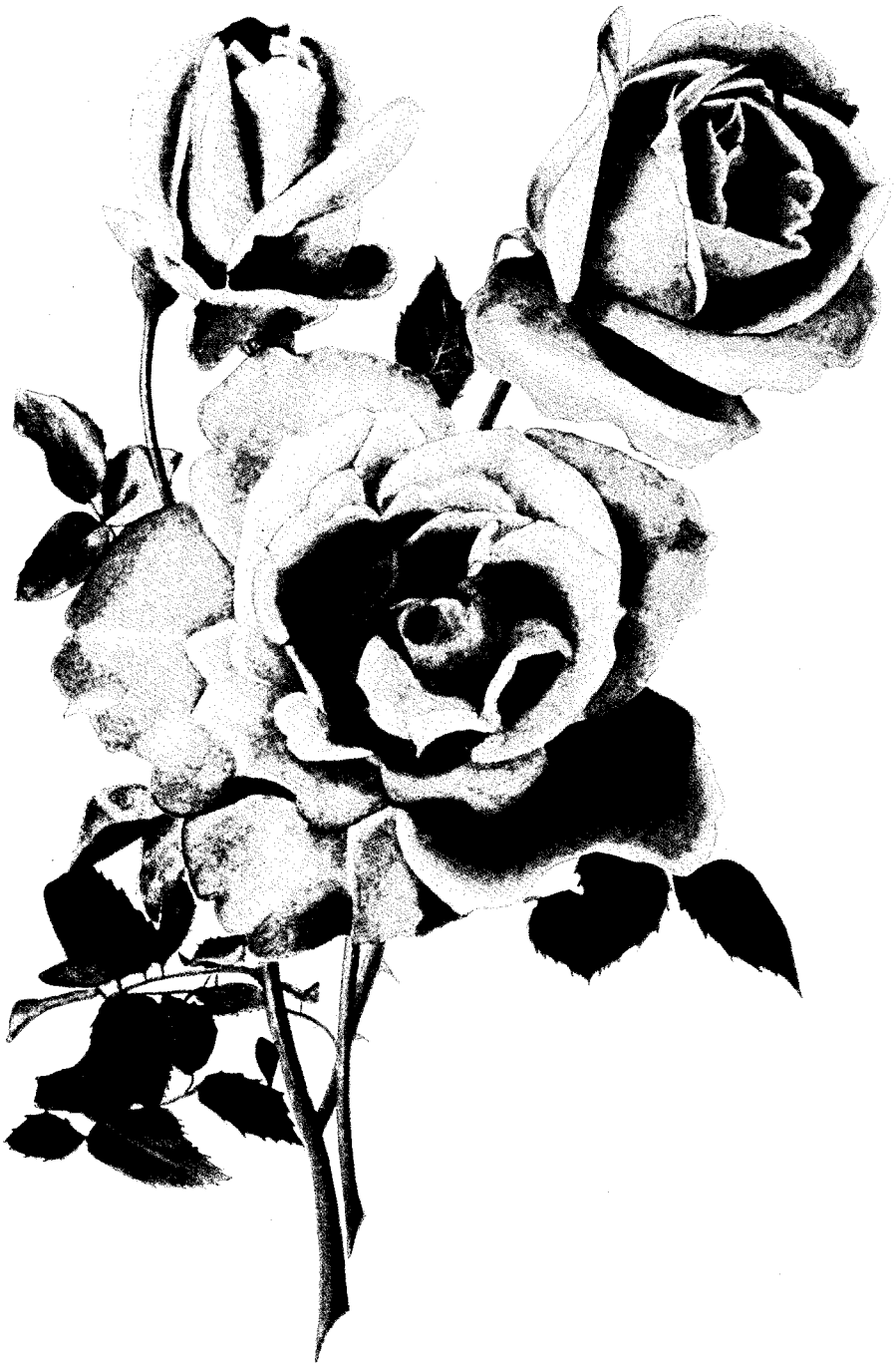
INVENTOR
Frederick Huber Howard
By Orville M. Kile
Plant Patent Agt.

Patented Feb. 11, 1941

Plant Pat. 447

UNITED STATES PATENT OFFICE

447

ROSE PLANT

Frederick Huber Howard, Montebello, Calif.

Application July 27, 1940, Serial No. 347,952

1 Claim. (Cl. 47—61)

My new variety of rose plant is of the hybrid tea class and is the result of crossing Mrs. J. D. Eislie by Crimson Glory. It has some of the features of each of its parents but is distinguished chiefly by its uniform rich crimson color of great brilliancy. Its flowers are of excellent form and fragrance and are produced profusely.

The new variety has been reproduced asexually and tested in a number of different localities and its outstanding characteristics have proved to be permanent.

The original illustrations accompanying this application show three specimens of the flowers of this variety in varying stages of opening and in approximately their true colors.

Following is a detailed description of this new variety, reference to color plates indicating Ridgway's Color Standards and Nomenclature.

*The plant*

Growth: Vigorous; upright; bushy; profuse bloomer.
Disease resistance: Very good.
Stems: Strong; stiff, long; Cerro Green (Plate V).
Thorns: Medium sized; hooked; pinkish-white; spaced irregularly and close together.
Foliage: Usually three to five leaflets, sometimes seven.
*Leaflets.*—Long and narrow, with acuminate apex; medium in size.
*Stipules.*—Narrow; clinging.

*The flower*

Bud:
*Size.*—Very large.
*Shape.*—Long; ovoid.
*Opening.*—Opens evenly; petals roll backward slightly.
*Peduncle.*—Short; smooth.
*Sepals.*—Five; simple; long.
*Color.*—Approximately Carmine (Plate I).
Blossom:
*Borne.*—Singly on long stems.
*Quantity.*—Abundant.
*Size.*—Large, frequently 5 or 6 inches across.
*Form.*—High centered, opening ragged.
*Petalage.*—Double, approximately 35 petals.
*Color.*—Commonly referred to as deep crimson-scarlet. With reference to Ridgway's chart, the color would be approximately Carmine (Plate I) to Spectrum Red (Plate I) but with more brilliance. The flowers hold their color without blueing.
Petals:
*Size.*—Outer petals about 1½ inches long and approximately the same in width. Inner petals much smaller.
*Shape.*—Almost round, with edges wavy and notched.
*Behavior.*—Cling until dry.
Longevity: Exceptionally lasting.
Fragrance: Moderate; delightful.
Reproductive organs:
*Pistils.*—Short; bunched; yellow.
*Stamens.*—Longer than pistils and surrounding them. *Filaments*—light yellow. *Anthers*—darker yellow.

Having thus disclosed my invention, I claim:

A new and distinct variety of hybrid tea rose plant, substantially as shown and described, characterized particularly by its prolific production; its vigorous growth; its disease-resistance; its large bud; and its large, fragrant, double blossoms of unfading, uniform, brilliant color approximately Carmine to Spectrum Red.

FREDERICK HUBER HOWARD.